United States Patent
Helgesson

(10) Patent No.: US 8,649,881 B2
(45) Date of Patent: Feb. 11, 2014

(54) SUTURE SLEEVE AND A METHOD FOR MANUFACTURING A SUTURE SLEEVE

(75) Inventor: Marcus Helgesson, Danderyd (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/322,612

(22) PCT Filed: May 28, 2009

(86) PCT No.: PCT/SE2009/000276
§ 371 (c)(1),
(2), (4) Date: Nov. 28, 2011

(87) PCT Pub. No.: WO2010/138028
PCT Pub. Date: Dec. 2, 2010

(65) Prior Publication Data
US 2012/0071959 A1    Mar. 22, 2012

(51) Int. Cl.
*A61N 1/05*    (2006.01)
(52) U.S. Cl.
USPC .......................... 607/149; 606/129; 604/174
(58) Field of Classification Search
USPC ........................... 607/116, 126; 604/174, 175
See application file for complete search history.

(56) References Cited

U.S. PATENT DOCUMENTS

| 4,553,961 | A | * | 11/1985 | Pohndorf et al. ............. 604/175 |
| 5,129,405 | A | | 7/1992 | Milijasevic et al. |
| 5,242,431 | A | | 9/1993 | Kristiansen |
| 5,628,780 | A | | 5/1997 | Helland et al. |
| 2004/0199234 | A1 | | 10/2004 | Rodriguez |
| 2004/0254623 | A1 | | 12/2004 | Rodriguez et al. |
| 2005/0137664 | A1 | | 6/2005 | Sommer et al. |
| 2006/0264803 | A1 | | 11/2006 | Lui et al. |
| 2009/0125059 | A1 | | 5/2009 | Verzal et al. |

FOREIGN PATENT DOCUMENTS

EP    0 218 128 A1    4/1987
WO    WO2009/120116 A1    10/2009

* cited by examiner

*Primary Examiner* — Eric D. Bertram

(57) ABSTRACT

A suture sleeve for securing a medical implantable lead in position in relation to a human or animal body, has a tubular body of a resilient material defining a through bore in the longitudinal direction of the suture sleeve and being formed with one or more longitudinal spaced, circumferential suture grooves on the outside and two or more grip enhancing projections around the inner circumference of the through bore in at least an area radially inward of a suture groove. The suture sleeve is formed with two or more stiffening protuberances in the bottom along the circumference of the suture groove such that the bottom of the suture groove deviates from circular as seen in cross section. The, stiffening protuberances are positioned radially outside of the respective grip enhancing projections on the inside. A method for manufacturing such a suture sleeve is also described.

8 Claims, 1 Drawing Sheet

SUTURE SLEEVE AND A METHOD FOR MANUFACTURING A SUTURE SLEEVE

BACKGROUND OF THE INVENTION

1. Field of the Invention

The invention relates to a suture sleeve for securing a medical implantable lead in position in relation to a human or animal body, of the type having a tubular body of a resilient material defining a through bore in the longitudinal direction of the suture sleeve and being formed with one or more longitudinal spaced, circumferential suture grooves on the outside and two or more grip enhancing projections around the inner circumference of the through bore in at least an area radially inward of a suture groove.

The invention also relates to a method for manufacturing of a suture sleeve.

2. Description of the Prior Art

Medical implantable leads are used for various purposes in order to connect the inner of a human or animal body with the outside or a device arranged subcutaneously. As examples of such leads can be mentioned electrical leads for monitoring and/or controlling of the function of a heart by means of a pacemaker or a cardiac defibrillator arranged subcutaneously, or a flexible tube for draining of liquid from the body or dispensing of drugs to a specific organ inside the body.

When implanting a lead into a body, it is common practice to arrange a suture sleeve around the lead which is formed as a tube of a resilient material and provided with one or more circumferential suture grooves on the outer surface. During implantation, the suture sleeve is positioned at an incision through a vein or some other kind of tissue formation and by means of a suture wire, positioned around tissue and the suture sleeve in the area of the suture groove, the suture sleeve can be fixated in relation to the tissue. At the same time the incision can be sealed by tying the tissue around the incision to the suture sleeve, and by tightening the suture wire the lead can be fixated to the suture sleeve by clamping of the inner surface of the bore through the suture sleeve against the outer surface of the lead due to the tightening action of the suture wire around the lead.

However, due to small lead dimensions and glossy outer surfaces of the leads having a low coefficient of friction, it can sometimes be difficult to fixate the lead properly inside the suture sleeve, since the suture wire cannot be tightened excessively due to the risk of cutting through tissue as well as the suture sleeve itself. A lead which is not properly fixated to the tissue may accidentally be pulled out, which can be devastating for its function since its inner end normally is in engagement with an organ to be controlled, treated or monitored. To overcome this problem, it is known in the art to arrange projections and the like on the interior sleeve surface at least in a region radially inward of each suture groove. In this way the gripping force, between the suture sleeve and the lead can be increased. Examples of such designs are disclosed e.g. in U.S. Pat. No. 5,129,405, US 2004/0254623 and US 2006/0264803. However, the effect, in terms of increased gripping force, of the suture sleeves disclosed according to the prior art, is not quite satisfactory.

SUMMARY OF THE INVENTION

It is an object of the invention to provide an improved suture sleeve by means of which the gripping force between the inner surface of the suture sleeve and the outer surface of the lead can be enhanced while maintaining the tightening force in the suture wire, alternatively maintaining the gripping force between the inner surface of the suture sleeve and the outer surface of the lead while lowering the tightening force in the suture wire.

The invention also relates to a method for manufacturing of a suture sleeve having essentially the same object as above.

Accordingly, the basis of the invention is the insight that the above object may be achieved by providing the inner bore of the suture sleeve with grip enhancing projections, at least in the area radially inward of each suture groove, and also provides stiffening protuberances within the suture grooves positioned radially outside of each gripping enhancing projection. In this way the tightening force in the suture wire will be distributed more directly to the grip enhancing projections on the inside of the suture sleeve while less force is distributed to the areas located in-between the grip enhancing projections.

Within this overall idea, the invention may be altered and modified in many different ways. Normally it is preferred, as in the hereinafter disclosed embodiment, to provide two suture grooves along the length of the suture sleeve. However, the suture sleeve could also be provided with only one suture groove or three or more suture grooves.

The invention is defined as being provided with at least two grip enhancing projections on the inside, but also more than two grip enhancing projections is conceivable within the scope of the invention, e.g. four as in the hereinafter described and illustrated embodiments. Generally, it is preferred to arrange an even number of grip enhancing projections in order to position them in pairs opposite each other on the inner circumference of the suture sleeve.

The grip enhancing projections on the inside may optionally be elongated and extending along a large portion of or the whole length of the suture sleeve, but may also be short and confined to the area closest to each suture groove. One disadvantage with having the grip enhancing projections extending the whole length of the suture sleeve is that with such a design it might be more difficult to achieve a fluid tight sealing between the suture sleeve and the lead. In the hereinafter described and illustrated embodiment, the grip enhancing projections are truncated conical in cross section. However, also other cross sectional shapes could be conceivable, such as an acute shape. The grip enhancing projections need not be formed as a continuous ridge formation but could also be formed as bosses or knobs arranged in series.

The stiffening protuberances in the bottom of each suture groove are preferably confined to the suture grooves only. Normally, the suture sleeve is formed as one uniform body comprised of only one elastic material and the stiffening protuberances are accordingly formed as a thicker material layer in the area radially outside of each grip enhancing projection having a different radius of curvature in cross section than the rest of the suture groove. Accordingly, the cross sectional shape of the suture sleeve at each suture groove will be non-circular, which will have to effect that the tightening force from the suture wire will be concentrated to the stiffening protuberances and transferred radially inwardly to the respective grip enhancing projection and the lead. However, it is also possible to position small embedment items, preferably of a more rigid material than the rest of the suture sleeve, in the mold before forming of the suture sleeve. In this way the stiffening protuberances may be formed of not only a thicker material but also of a material having e.g. a larger strength.

To further increase the concentration of the tightening forces from the suture wire to the grip enhancing projections, it is conceivable to arrange weakening zones in the areas between adjacent grip enhancing projections and stiffening protuberances. In a hereinafter described and illustrated embodiment, these weakening zones are provided with weakening grooves or recesses such that the wall of the suture sleeve is provided with a thinner material thickness in these weakening zones and hence will be easier deformed when tightening the suture wire.

A suture sleeve according to the invention may be combined with numerous other features. For example, the invention may be combined with the features disclosed in the PCT application WO 2009/120116 where a portion of the bore through the suture sleeve is formed with a non-circular cross section such that the through bore will clamp around the lead. Preferably, the non-circular bore portion can be positioned centrally of the suture sleeve while the suture grooves, being provided with grip enhancing projections and stiffening protuberances according to the present invention, can be positioned on each side of the non-circular bore portion. The suture sleeve can also be provided with an axial slit through the suture sleeve wall in order to facilitate threading of the suture sleeve onto a lead, as is previously well known in the art.

DESCRIPTION OF THE PREFERRED EMBODIMENTS

Figure 1:
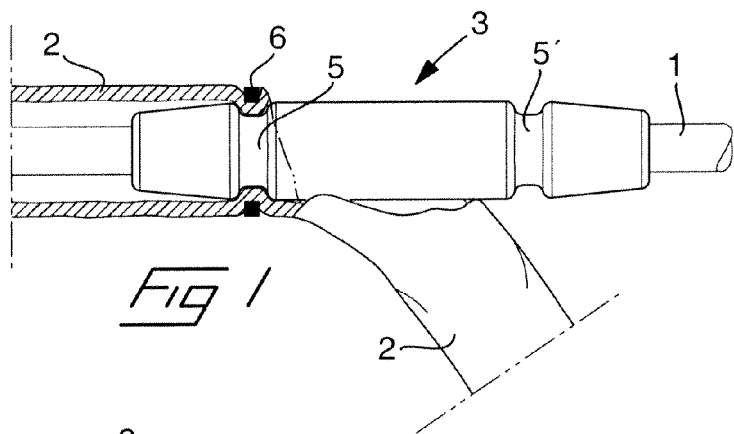
FIG. 1 is a side view, partly in section, through a lead inserted into a vein by means of a suture sleeve according to the invention.
Figure 2:
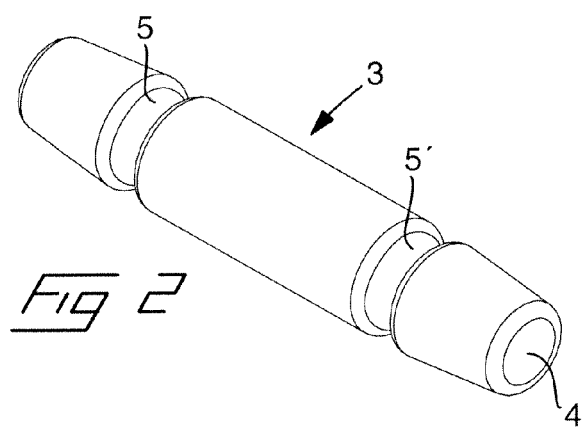
FIG. 2 is perspective view of the suture sleeve of FIG. 1.
Figure 3:
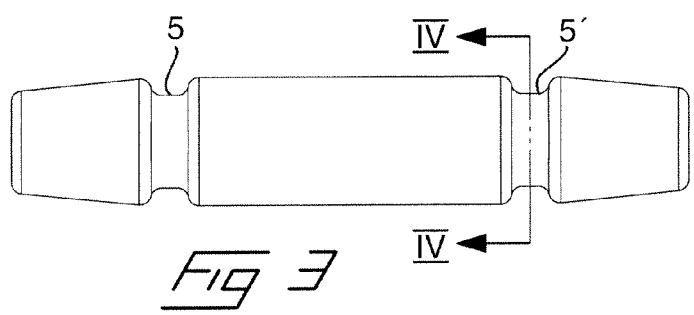
FIG. 3 is a side view of the suture sleeve of FIGS. 1 and 2.

Reference is first made to FIG. 1 in which is illustrated implantation of a lead 1 through a vein 2 by means of a suture sleeve 3 according to the invention. The suture sleeve is illustrated more in detail in the perspective view and the side view of FIGS. 2 and 3, respectively, and is formed as an elongated tube of an elastic material provided with an inner through bore 4 which extends in the longitudinal direction of the sleeve. On the outside the suture sleeve is formed with two circumferential and longitudinally spaced suture grooves 5, 5'. When using the suture sleeve for implanting a lead into a vein 2, as illustrated in FIG. 1, an incision is made in the vein and subsequently the lead 1 together with an end portion of the suture sleeve 3 is inserted through the incision into the vein, as is illustrated in FIG. 1.

By tying a suture wire 6 around the vein 2 and the suture sleeve 3 in a region at one of the suture grooves 5, the suture sleeve will be fixated to the vein and the region between the inside of the vein and the outside of the suture sleeve will be fluid tight sealed. To further increase the fixation of the suture sleeve, it is possible to tie a second suture wire (not shown) around the suture sleeve and through adjacent tissue, such as muscles or the like, in the region of the second suture groove 5'.

As described above, the suture sleeve and the method for implanting a lead to a body is known in the art. However, with the state of the art suture sleeves it is not certain that the fixation of the lead inside the suture sleeve will be sufficient, since during implantation the lead must be displaceable inside the suture sleeve and the suture wire cannot be tightened too excessively since that would risk cutting through the tissue positioned between the suture wire and the suture groove.

Figure 4:
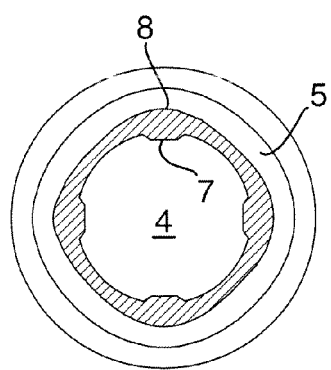
FIG. 4 is a cross section, taken along line IV-IV in FIG. 3, of the suture sleeve in accordance with the invention in the region of the suture groove, showing a first embodiment of the suture sleeve.

To overcome this problem, the suture sleeve according to the invention is arranged such that the tightening forces from the suture wire will be more directly transferred to the lead. This is accomplished, as is illustrated in the cross section through one of the suture grooves in FIG. 4, by providing the suture sleeve 3 with grip enhancing projections 7 on the inside surface of the through bore 4. Accordingly, when tying a suture wire around the suture sleeve, the tightening force from the suture wire will be concentrated to the grip enhancing projections 7. In order to further concentrate the tightening force from the suture wire to the grip enhancing projections, the suture sleeve according to the invention is provided with stiffening protuberances 8 in the bottom of the suture groove 5, 5' in an area radially outside of each grip enhancing projection 7 on the inside. In this way the outer cross-sectional shape of the suture sleeve in the bottom of the suture groove 5, 5' will be non-circular, as is visible in FIGS. 4 and 5. This feature in combination with the feature that the stiffness of the suture sleeve will be increased in the region of each grip enhancing projection 7 due to the increased material layer at the stiffening protuberances 8, will further concentrate the tightening force from the suture wire to the grip enhancing projections.

Figure 5:
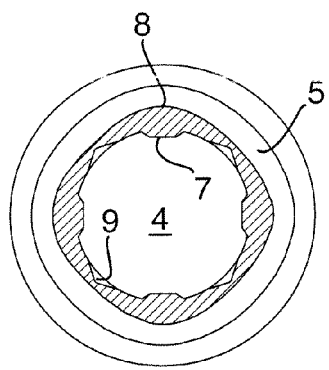
FIG. 5 is a cross section according to FIG. 4 of a second embodiment of the suture sleeve of the invention.

FIG. 5 illustrates, in a cross-sectional view through one of the suture grooves 5, 5', a second embodiment of a suture sleeve according to the invention. This embodiment corresponds to the embodiment according to FIG. 4 except that in this embodiment the suture sleeve is provided with weakening formations in form of grooves or recesses 9 radially inward of each suture groove on the inside surface of the bore 4 in the region between each stiffening protuberance 8. In this way the wall portion of the suture sleeve will be weakened and more easily deformable, which will concentrate the tightening forces from the suture wire even more to the grip enhancing projections 7 and press them toward the lead. It is to be understood that the weakening formations 9 can be realized in many different ways and also can be formed in the outside surface at the bottom of the suture grooves.

Although modifications and changes may be suggested by those skilled in the art, it is the intention of the inventor to embody within the patent warranted heron all changes and modifications as reasonably and properly come within the scope of his contribution to the art.

I claim as my invention:

1. A suture sleeve comprising:

a tubular body comprised of resilient material, said tubular body having a longitudinal axis and having a bore extending through said tubular body along said longitudinal axis, said bore being configured to receive a medical implantable lead therein;

said tubular body having a body exterior surface having at least one suture groove therein, said exterior body surface being configured for insertion in a body lumen of a living subject and said suture being configured to allow a suture to be tied around said suture groove, with said lumen between said suture and said suture groove, to hold said suture sleeve, and said medical lead in said bore thereof, in place relative to said body lumen;

said tubular body comprising at least one grip enhancing projection projecting into said bore radially inwardly of said suture groove to promote gripping of said medical implantable lead in said bore; and a stiffening protuberance in said tubular body between said suture groove and said grip enhancing projection, said stiffening protuberance longitudinally confined to only a longitudinal width of said suture groove, and said stiffening protuberance giving said suture sleeve a non-circular cross-section in a plane orthogonal to said longitudinal axis;

wherein said suture groove has a proximal end and a distal end, and wherein said stiffening protuberance longitudinally extends from the proximal end of the suture groove to the distal end of the suture groove, and wherein said stiffening protuberance proximally terminates in the longitudinal direction at the proximal end of the suture groove and distally terminates in the longitudinal direction at the distal end of the suture groove.

2. A suture sleeve as claimed in claim 1 wherein said grip enhancing projection forms a truncated cone in said cross-section.

3. A suture sleeve as claimed in claim 1 wherein said suture groove has a radius of curvature in said cross-section, and wherein said stiffening protuberance has a radius of curvature in said cross-section that differs from said radius of curvature of said suture groove in said cross-section.

4. A suture sleeve as claimed in claim 1 comprising a plurality of stiffening protuberances proceeding circumferentially around said suture groove and said bore, and wherein said tubular body comprises a wall portion in a region between two adjacent stiffening protuberances and comprising a weakening formation.

5. A suture sleeve as claimed in claim 1 wherein said stiffening protuberances are formed by molding reinforcement elements into material of said tubular body.

6. A suture sleeve as claimed in claim 1 wherein said at least one grip enhancing projection is longitudinally configured to an area closest to said suture groove.

7. A method for manufacturing a suture sleeve comprising:
    forming a tubular body of resilient material with a bore extending therein along a longitudinal axis of said tubular body;
    forming at least one circumferential suture groove at an exterior of said tubular body;
    forming at least one grip enhancing projection in said bore of said tubular body that projects into said bore in a plane containing said suture groove; and
    molding embedment items into said suture sleeve material to form stiffening protuberances in said tubular body between said grip enhancing projection and said suture groove, giving said suture groove a non-circular cross-section in a plane orthogonal to said longitudinal axis;
    wherein said embedment items are longitudinally confined to only a longitudinal width of said suture groove; and
    wherein said suture groove has a proximal end and a distal end, and wherein said embedment items longitudinally extend from the proximal end of the suture groove to the distal end of the suture groove, and wherein said embedment items proximally terminate in the longitudinal direction at the proximal end of the suture groove and distally terminate in the longitudinal direction at the distal end of the suture groove.

8. A method as claimed in claim 7 wherein said at least one grip enhancing projection is longitudinally confined to an area closest to said suture groove.

* * * * *